United States Patent

Ishizuka et al.

[11] Patent Number: 5,227,765
[45] Date of Patent: Jul. 13, 1993

[54] COUNTING AND MEASURING APPARATUS FOR MEDICAL CLOTHS

[75] Inventors: Hiroaki Ishizuka; Masaaki Numazawa; Kenichi Kurano, all of Tokyo, Japan

[73] Assignee: Senko Medical Instrument Mfg. Co. Ltd., Tokyo, Japan

[21] Appl. No.: 721,977

[22] Filed: Jun. 27, 1991

[30] Foreign Application Priority Data

Apr. 12, 1991 [JP] Japan .................. 3-033551[U]
May 7, 1991 [JP] Japan .................. 3-041248[U]

[51] Int. Cl.⁵ .................................. G08B 13/14
[52] U.S. Cl. .................. 340/568; 250/223 R; 340/556; 340/666
[58] Field of Search ........ 340/568, 573, 666, 555–557, 340/674, 522, 526, 529; 250/223 R, 222.1, 564–565; 377/6; 604/404; 206/362, 370, 438; 177/45, 245; 356/427, 436, 436–439, 385–387, 338; 141/94, 331; 222/23

[56] References Cited

U.S. PATENT DOCUMENTS

| | | | |
|---|---|---|---|
| 3,211,195 | 10/1965 | Porter | 141/331 X |
| 4,384,280 | 5/1983 | Haag | 340/556 |
| 4,555,624 | 11/1985 | Steffen | 250/223 R |
| 4,592,397 | 6/1986 | Mitzner | 141/94 X |
| 4,742,339 | 5/1988 | Baziuk | 340/568 |
| 4,866,425 | 9/1989 | Lindmark | 340/556 |
| 4,887,715 | 12/1989 | Spahn et al. | 206/370 |

FOREIGN PATENT DOCUMENTS

| | | | |
|---|---|---|---|
| 975855 | 10/1975 | Canada | 340/674 |
| 170984 | 2/1986 | European Pat. Off. | 250/222.1 |
| 853499 | 8/1981 | U.S.S.R. | 250/564 |

Primary Examiner—Thomas Mullen
Attorney, Agent, or Firm—Kane, Dalsimer, Sullivan, Kurucz, Levy, Eisele and Richard

[57] ABSTRACT

An apparatus for counting used medical cloths and measuring the quantity of liquid absorbed therein is disclosed. The apparatus comprises a hollow passage way for passing the medical cloths therethrough, an entrance portion for guiding the medical cloths to the passage, a pass detection sensor arranged in the passage for sensing the medical cloths, a weight sensor disposed at the bottom of the passage for sensing weight of dropped medical cloths, and a control unit for operating the output signals of the pass detection sensor and the weight sensor to output the number of dropped medical cloths and the weight of liquid absorbed therein. The control unit comprises a judging element for judging whether counting condition is normal or not according to the TSR of output signals of the sensors. The apparatus further comprises an alarm element for producing alarm signals when the judging element judges the condition abnormal.

20 Claims, 11 Drawing Sheets

COUNTING AND MEASURING APPARATUS FOR MEDICAL CLOTHS

BACKGROUND OF THE INVENTION

The present invention relates to a counting and measuring apparatus for counting medical cloths used in a medical field, for example, in a surgical operation.

PRIOR ART

In surgical operations, medical cloths or gauzes are used at a relevant place of a human body in order to absorb blood or other body fluids thereof. Since these gauzes must not be left in the human body when the operation is finished, the number of the used gauzes are carefully checked whether it is identical with the initial count.

It is also necessary for a surgeon to know the amount of blood absorbed in the used gauzes during the surgery because excessive of bleeding could be fatal to the patient.

Figure 22:
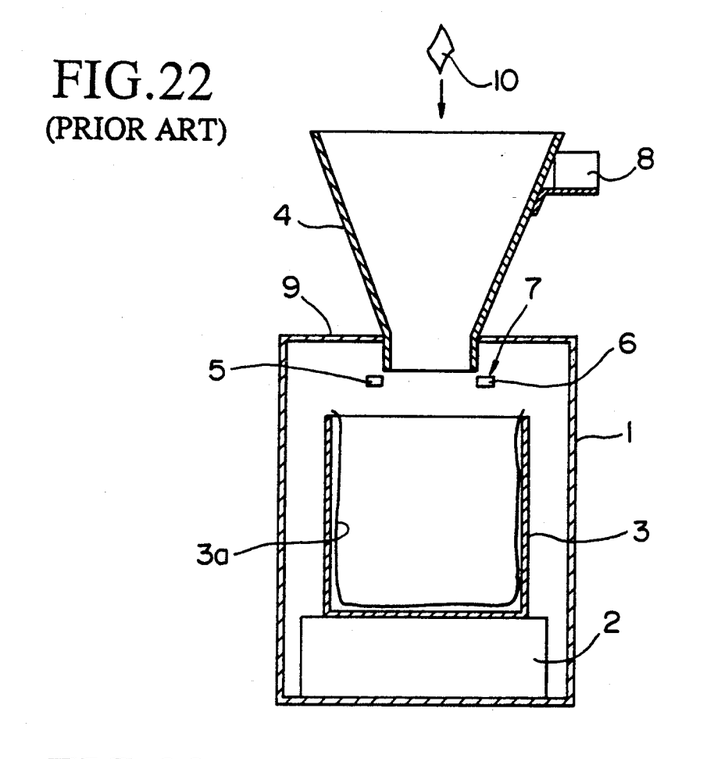
FIG. 22 is a cross-sectional elevational view of the conventional apparatus.
Figure 23:
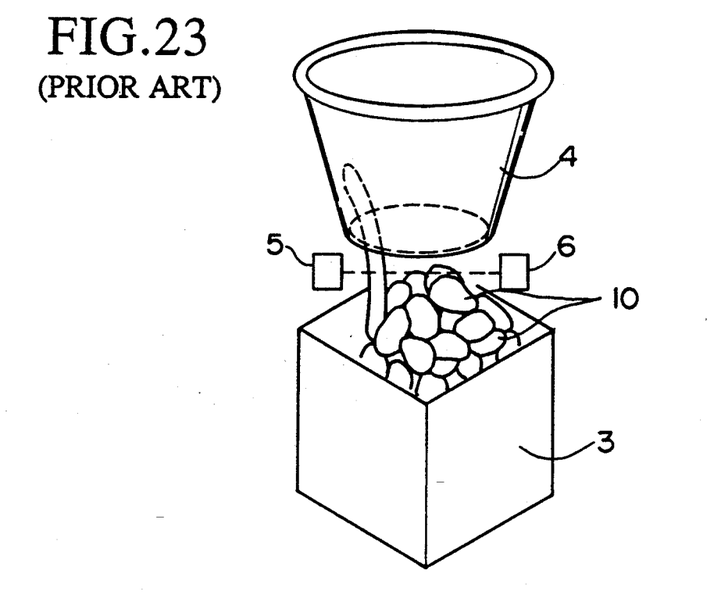
FIG. 23 is a perspective view of the apparatus of FIG. 22.

In order to count the number of used gauzes and to measure the amount of absorbed blood therein, an apparatus illustrated in FIGS. 22 and 23 is conventionally used. This apparatus is comprised of an envelope 1, a weighing table 2 disposed at the bottom of the envelope 1, a container 3 disposed on the weight sensing means for receiving used gauzes 10 via a bag 3a installed therein, a hopper 4 disposed at a center hole of an upper plate 9 covering the envelope 1 for forming a hollow passage for used gauzes 10 dropping into the container, and an optical sensor 7 disposed below the hopper 4 for sensing the falling of gauzes 10. The optical sensor 7 is comprised of a light projector 5 and a light receiver 6 arranged at opposite side of the hollow passage so as to face each other. The apparatus further comprises a display device 8 and a micro computer (not shown) electrically connected to the weighing table 2, the optical sensor 7 and the display device 8.

The apparatus is used as described below. Prior to a surgical operation, the number of prepared gauzes are counted. During the surgical operation, an assistant person such as a nurse (an operator) picks up used gauzes 10 from the body and drops them into the hopper 4 one by one. The optical sensor 7 senses each falling gauze 10 and outputs a signal to the micro computer. The weighing table 2 senses the total weight container 3 including the bag 3a and the used gauzes 10. The micro computer counts the number of used gauzes 10 from the output signal of the optical sensor 7. Then, the micro computer calculates the dry weight of gauzes 10 in the container 3 by multiplying the unit dry weight of gauze 10 by the number of gauzes. Further, the micro computer calculates the amount of blood absorbed in the gauzes 10 by subtracting the weight of the container 3, bag 3a and the dry gauzes 10 from the total weight indicated by the weighing table 2. These results, i.e., the number of the used gauzes 10 and the weight of blood, are displayed on the display unit 8 so as to be recognized by the operator. The volume of blood is calculated by dividing the above value by the specific gravity of blood, 1.06 g/cc. The surgeon keeps track of the amount of blood indicated at the display unit 8 during the surgery. When the surgery is over, and the number of gauzes 10 are confirmed, the bag 3a including the gauzes 10 is extracted from the envelope 6 and processed for disposal.

However, the prior art described above has disadvantages as described below. The optical sensor 7 senses a dropping object when it interrupts a light beam of the light projector 5. Therefore, when a gauze 10 drops in the vicinity of the inner surface of the hopper 4, it may not interrupt a light beam and therefore may be missed by the sensor 7. One way to prevent such a situation, is to provide a plurality of sensors 7, i.e., plurality of pairs of light projector 5 and light receiver 6. Another way is to decrease the area of the lower aperture (opening) of the hopper 4. However, if the first way is used the equipment cost will rise. For the latter way, if the area of the upper aperture of the hopper 4 remains the same, the taper of the hopper 4 increases and the gauze 10 may stick to the inner surface of the hopper 4.

When the gauze 10 stick to the inner surface of the hopper 4 and stay there, it does not interrupt the light beam so that it is not counted resulting in a counting error. Alternatively if it hangs down from the hopper 4, it cuts the light beam off and the sensor 7 is no longer possible operational. In these cases, it is necessary for the operator to remove a sticking gauze 10 from the inner surface of the hopper 4 and drop it. However, since the sensor 4 cannot distinguish a human hand from dropping gauze 10, may count wrong.

Further, especially when the aperture of the hopper 4 is narrow, gauzes 10 may not distribute uniformly in the bottom of the container 3, and they may pile up to a certain height. In such a case, they may cut off the light beam and the sensor 7 is no longer operationed to sense in the same way as described above.

Another disadvantage of the conventional apparatus occurs when a gauze 10 is saturated blood. The optical sensor 7 senses an object when the objects interrupts the light beam, that is, when the output of the light receiver turns from "on" to "off" and again "on". Therefore, if blood dips from a gauze 10 down into the container 3, it is counted as a dropping gauze 10.

An object of the provide invention is, therefore, to present a counting and measuring apparatus capable of judging whether the apparatus is operational or not. The apparatus produces an alarm signal when it judges that the condition is in operational, or produces an output signal for correcting the calculated values according to the judgment.

Another object of the invention is to present an apparatus capable of identifying what kind of object is sensed so that it can sound on alarm when the object is to be judged abnormal. If the apparatus receives an unexpected object, it examines whether an object is a drop of blood or not. If it judges that it received a blood drop, it does not count it as a gauze 10 but take the weight of blood into account.

SUMMARY OF THE INVENTION

The present invention has been done to accomplish the object mentioned above, and is directed to an apparatus for counting a dropping object comprising:

an envelope defining a hollow passage for passing dropping objects therethrough;

a plurality of sensors disposed at said passage at a vertical distance therebetween for sensing said dropping objects;

a counting means for counting said dropping object according to the output signals of said sensors;

a judging means for judging whether counting condition is normal or not according to the time series relationship of output signals of said sensors; and an alarm means for producing alarm signals when said judging means judges that the condition is abnormal.

In one type of an embodiment, the sensors are composed of a plurality of pass detection sensors disposed midway in the passage. In another type of an embodiment, the sensors include a pass detection sensor disposed in midway of the passage and a weight sensor at the bottom of the passage. The pass detection sensor is usually an optical sensor comprising a light projector and a light receiver located at opposite sides of the passage to each other. When the light from the light projector is temporarily interrupted and again received, the remote sensor senses a passing object and outputs a detection signal. By applying a reflecting means at the hollow passage for reflecting light from the light projector to the light receiver, the light beam can scan a wider area without increasing the number of light projectors or the light receiver.

The result acquired by the counting means is displayed by a display means so that an operator can see it.

The judging means can judge many types of data acquired by the sensors, for instance, an of interval of time between sensing of the upper and lower sensors, or a time interval when the light receiver does not receive light from the light projector.

Another invention is directed to an apparatus for counting used medical cloths and measuring the quantity of liquid absorbed therein comprising;

an envelope defining a hollow passage for passing said medical cloths therethrough;

an entrance portion for guiding said medical cloths to said passage;

a pass detection sensor arranged at said passage for sensing said medical cloths;

a weight sensor disposed at the bottom of said passage for sensing weight of dropped medical cloths;

control unit for operating the output signals of said pass detection sensor and said weight sensor to output the number of said dropped medical cloths and weight of liquid absorbed therein, said control unit comprising a judging means for judging whether counting condition is normal or not according to the time series relationship of output signals of said sensors; and an alarm means for producing alarm signals when said judging means judges the condition abnormal.

It is possible to provide the control unit with a function to correct the number of the medical cloths when it judges that the condition is abnormal.

DESCRIPTION OF THE PREFERRED EMBODIMENTS

The preferred embodiment of the present invention will be described below.

FIGS. 1 to 9 depict a first embodiment of the present invention. Numeral 11 depicts an envelope having a side door 13 arranged at one side thereof for extracting used gauzes 12 therefrom. A cap or an upper plate 14 is detachably mounted on the envelope 11. Casters 15 are provided under the envelope 11 for transportation of the apparatus. A weighing table 16 is provided at the bottom of the envelope 11, comprising a weight sensor (a load cell) 16a. A container 25 including a bag 23 is disposed on the weighing table 16.

Figure 1:
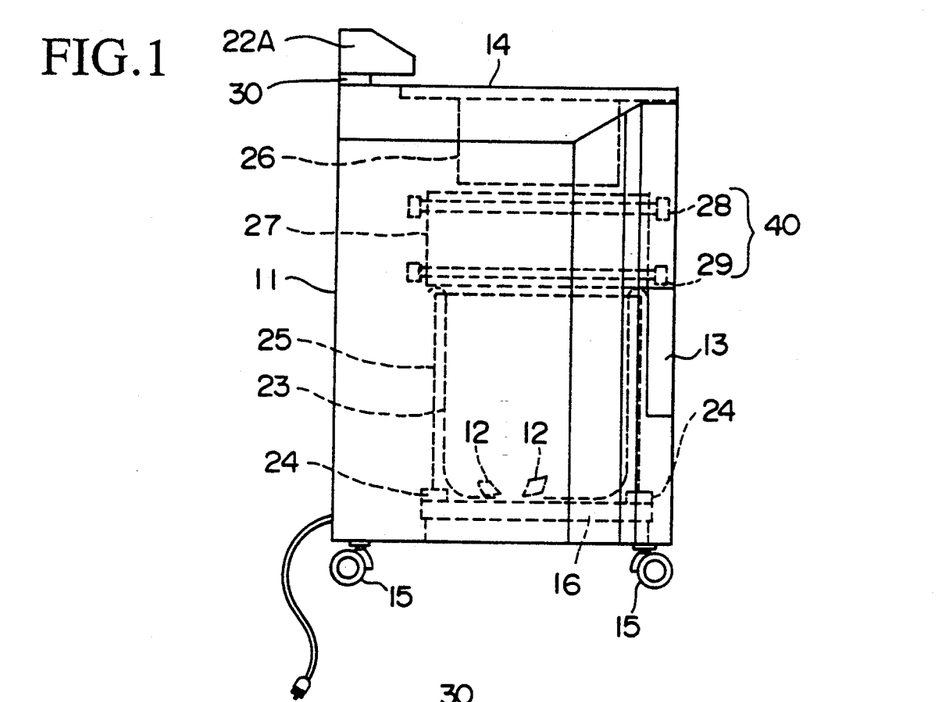
FIG. 1 is a side elevational view of an apparatus according to the present invention.
Figure 2:
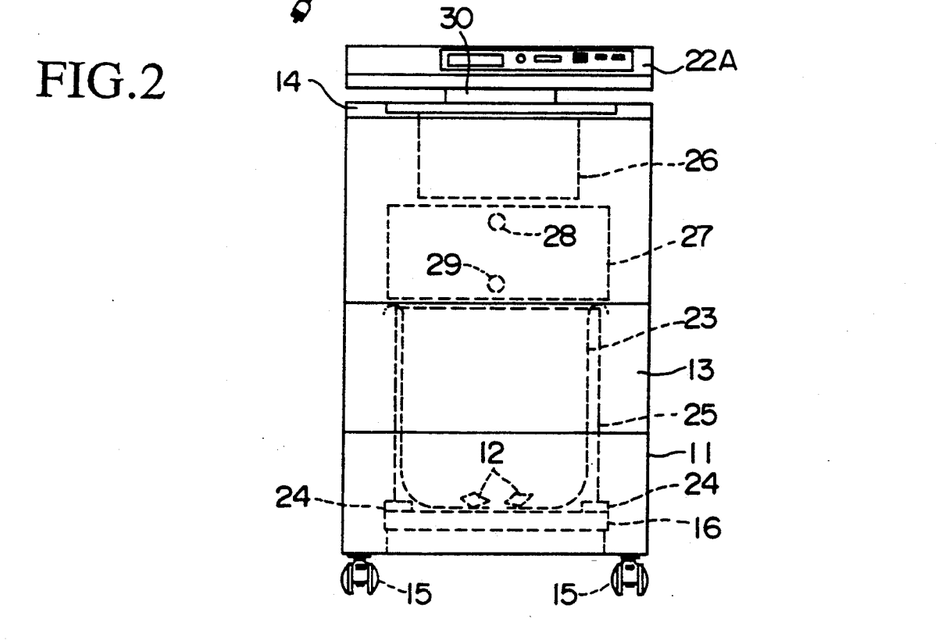
FIG. 2 is a front elevational view of an apparatus shown in FIG. 1.
Figure 3:
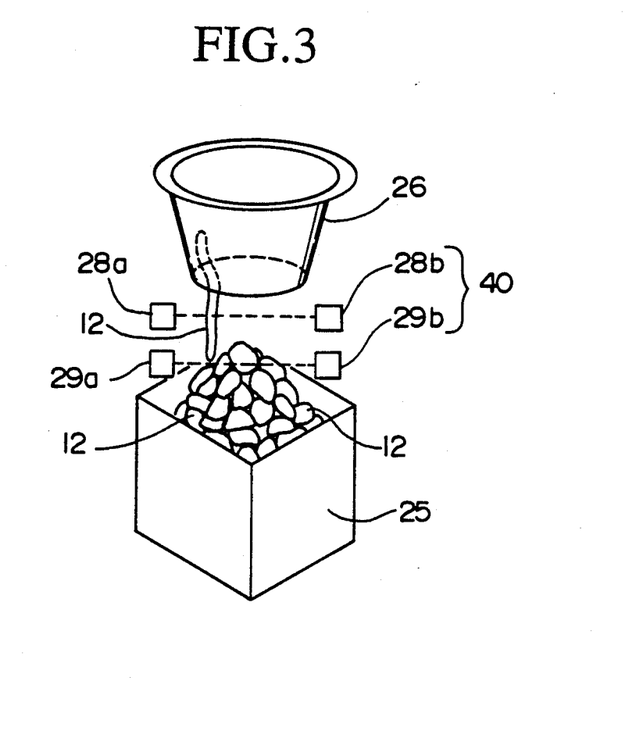
FIG. 3 is a perspective view schematically illustrating the hopper and the container.

Several positioning elements 24 are fixed on the weighing table 16 for positioning and securely holding a container 25. The container 25 is of a rectangular parallelepiped shape. The bag 23 is also formed in a rectangular parallelepiped shape when unfolded, and is made from synthetic resin such as polyethylene or polypropylene. The bag 23 is installed in the container 25 so as to expand therein with its edge portion being pulled out of the container's upper edge and suspended thereto. A pull string (not shown) is sewn in along the edge of the bag 23 so as to be able to close the aperture by pulling the string. This bag 23 is sized so that it is about 250 mm square at the aperture and 500 to 550 mm deep when unfolded, and is capable of storing 150 gauzes 12 for surgical use (about 300 mm square). This is an amount of gauzes 12 necessary for an operation of heart when bleeding is maximum.

Figure 5:
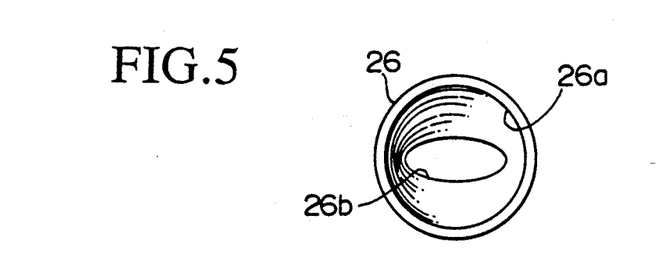
FIG. 5 is a plan view of the hopper as shown in FIG. 2.
Figure 6:
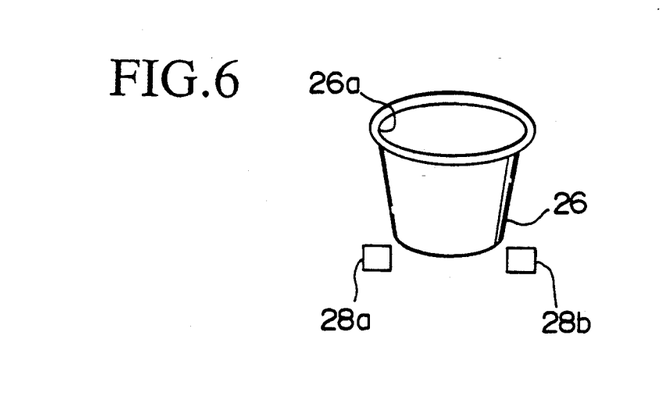
FIG. 6 is a perspective view of the hopper shown in FIG. 1.

A hopper 26 or an entrance portion is provided at the upper plate 14. The hopper 26 is cylindrically formed, and is tapered so that the upper portion has a larger cross-sectional area than the lower portion. The top aperture 26a of the hopper 26 is circular and the bottom aperture 26b is elliptical.

A guiding member 27 formed in a cylindrical shape and having a larger diameter than the container 25 is provided between the hopper 26 and the container 25 for guiding dropping gauzes 12. The hopper 26 and the guiding member 27 define a hollow passage for dropping objects in the envelope 11.

Figure 7:
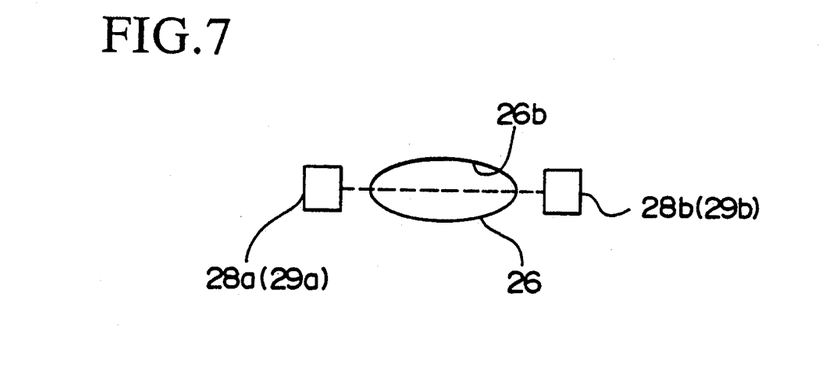
FIG. 7 is a plan view of the hopper and the pass detection sensor of FIG. 1.

A pass detection sensor 40 is provided at the passage for detecting an object possing therethrough. The pass detection sensor 40 comprises an upper sensor 28 and a lower sensor 29 spaced at a vertical distance to each other. Each of the sensor 28, 29 is arranged at the outside the guiding member 27 on a supporting member (not shown). These sensors 28, 29 are respectively comprised of a light projector 28a, 29a and a light receiver 28b, 29b arranged at opposite sides of the passage in a face to face relationship on the same horizontal line. Several apertures (not shown) are formed on the guiding member 27 so that lights from the light projector 28a, 29a can pass therethrough. With such construction, when a used gauze 12 passes through the lower aperture 26b of the hopper 26, it necessarily interrupts the light of both upper and lower sensors 28, 29.

The dimension of the opening of the bag 23 is set so that it is considerably larger than that of the bottom end 26b of the hopper 26. The apparatus of the present embodiment further comprises a level sensor (not shown) analog level of the weighing table 16 and an level adjusting means (not shown) for adjusting the level thereof.

Figure 8:
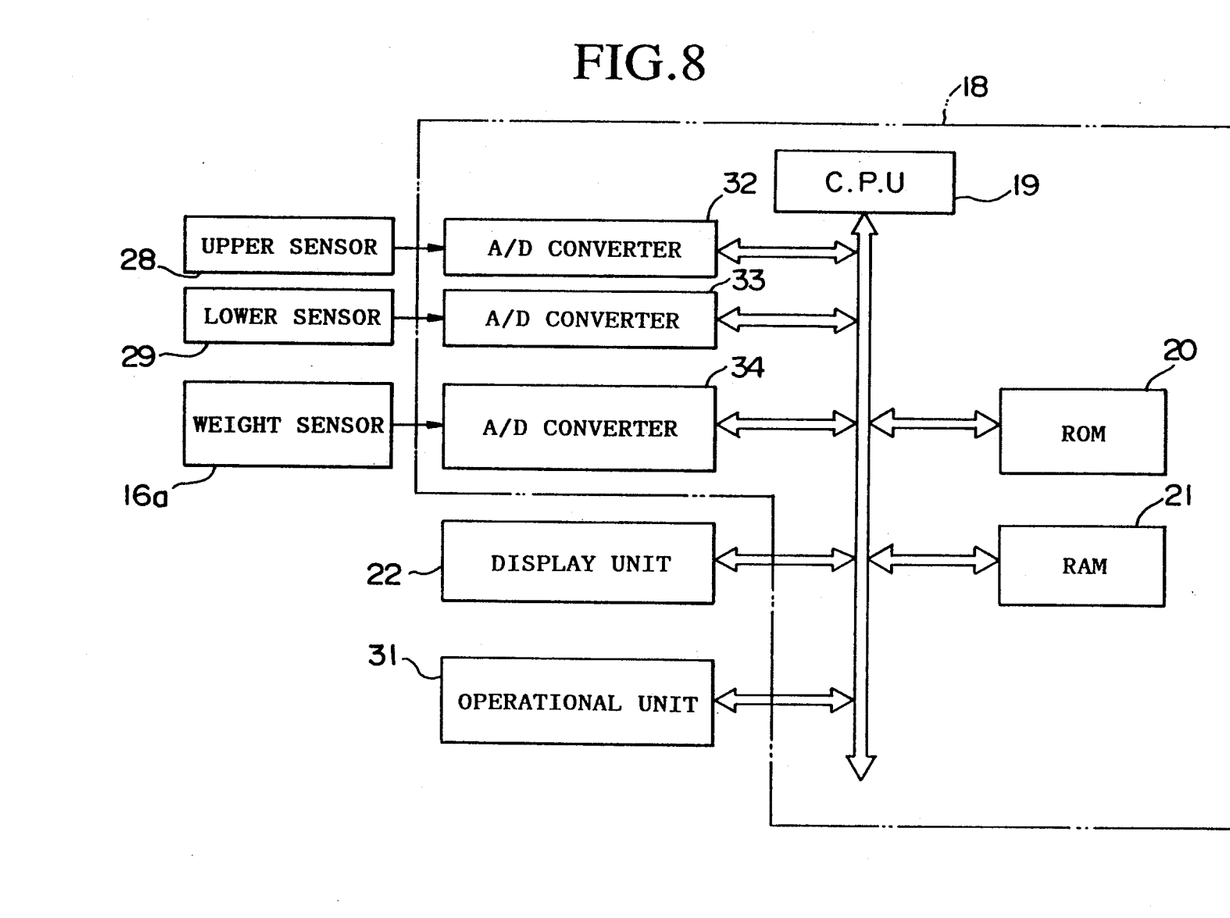
FIG. 8 is a schematic diagram of the controlling system of the apparatus of FIG. 1.

FIG. 8 depects a control unit 18 for controlling the apparatus, comprising a central processor unit (CPU) 19, a ROM 20, a RAM 21 and analog-digital converters 32, 33, 34. A display unit 22 and an operational unit 31 are respectively connected to the CPU 19 via a bus line, and an upper sensor 28, a lower sensor 29 and the weight sensor are respectively connected to the CPU 19 via the analog-digital convertors 32, 33, 34 and the bus line. The ROM 20 is installed with a controlling program. The RAM 21 is used for a working area for the CPU 19. The CPU 19 performs computations and comparisons on the signals from the sensors 16a, 28, 29. The RAM 21 also simulates various types of registers. The display unit 22 displays the outputs of the CPU 21, i.e., number of gauzes 12 dropped in the container 25, the total weight and total volume of blood absorbed in the used gauzes 12.

Figure 4:
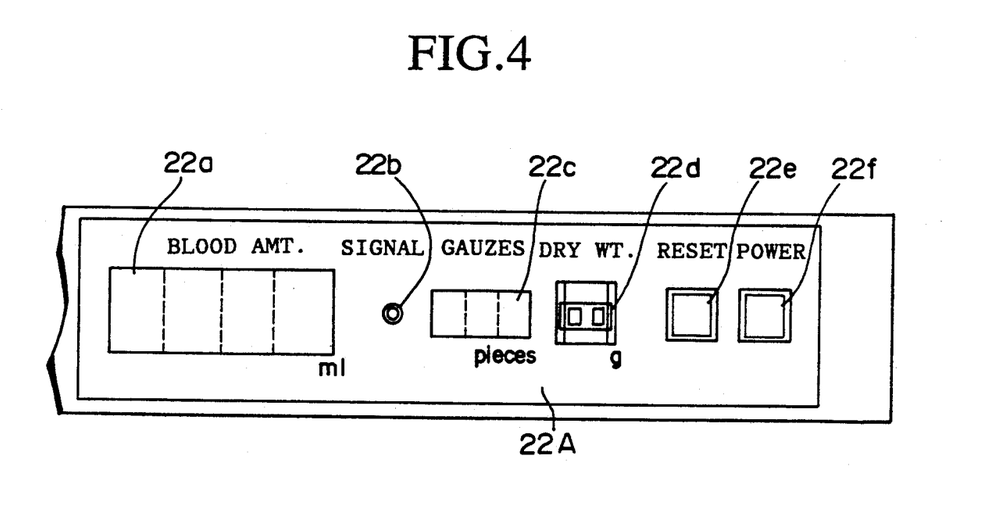
FIG. 4 is a partial enlarged view of the control panel as shown in FIG. 1.

The display unit 22 and the operational unit 31 are provided in a control panel 22A on the upper plate 14 by a supporting member 30. The display unit 22 comprises a blood amount indicator 22a for indicating the amount of blood absorbed in the gauzes 12, a counting light 22b which flickers when the CPU 19 counts a gauze 12 and which is on continuously lighting when the CPU 19 produces an alarm signal for warning, a count indicator 22c for indicating the number of gauzes 12 dropped in the container 25, a dry weight indicator 22d for setting and indicating the dry weight of a gauze 12. The control panel 22A also comprises a resetting switch 22e and a power switch 22f. The operational unit 31 comprises a tare weight setting portion 22g for setting the weight of the container 25 and the bag 23.

Figure 9:
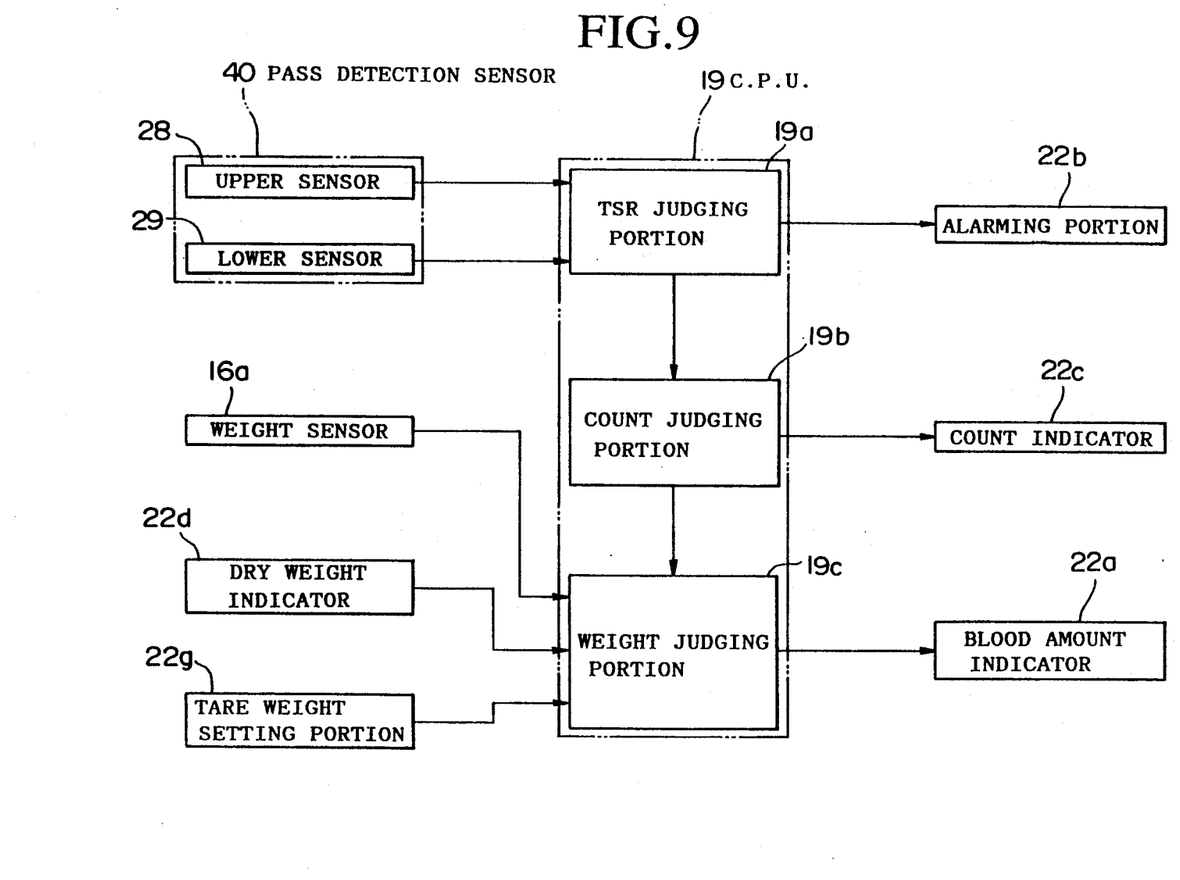
FIG. 9 is a schematic diagram showing a relationship of the controlling system shown in FIG. 8.
Figure 10:
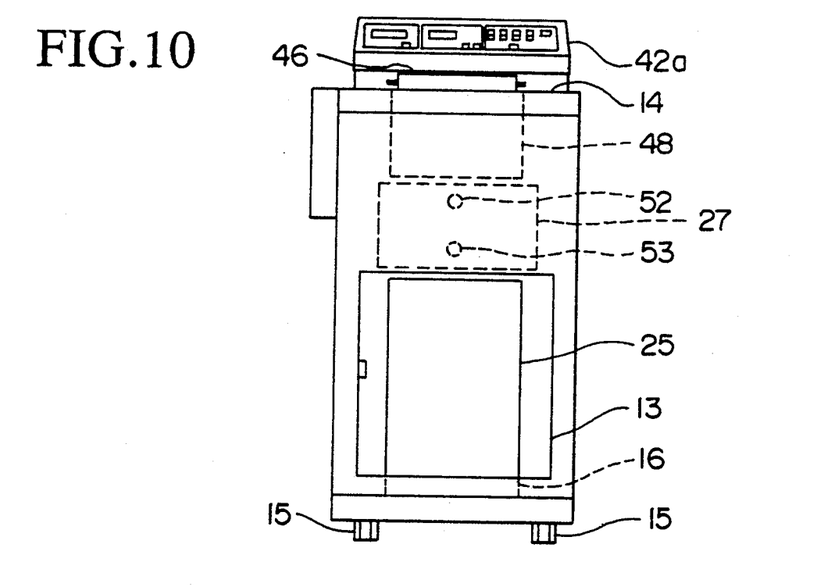
FIG. 10 is a front elevational view of the second embodiment according to the present invention.

The function of the CPU 19 is described below with reference to the FIG. 9, which is a schematic diagram of the control system of the apparatus.

When the light from the light projector 28a, 29a is interrupted, the upper or lower sensor 28, 29 sense an object and output a detection signal. The CPU 19 detects the time series relationship (TSR) of the detection signals from the upper and lower sensors 28, 29 at a TSR judging portion 19a. The CPU 19 counts the detection signals at a counting portion 19b when the TSR is determined to be normal. The CPU 19 further calculates the weight of blood absorbed in the gauzes 12 at a weight calculating portion 19c in accordance with the data from the counting portion 19b, the weight sensor 16a, the dry weight indicator 22d and a tare weight setting portion 22g.

Further, the CPU 19 produces an alarm signal to the alarm device 22b when it determines that the condition of the apparatus is abnormal such as when a used gauze 12 interrupts the light of only one of the upper and lower sensors 28, 29, or when the time interval between detections (TSR) of the two sensors is longer than a predetermined value (0.5 sec for example).

The usage of the apparatus of the embodiment in a case of surgical operation is described below.

It is ascertained in advance that the weighing table 16 is level. The data such as dry weight of the prepared gauze 12, weight of the container 25 and the bag 23 are entered through the operational unit 31 so as to record them on the RAM 21.

During the surgical operation, an assistant person such as a nurse (an operator of the apparatus) picks up used gauzes 12 from the surgical field, and drops them into the hopper 26 one by one with a hand covered by a glove. The gauze 12 first interrupts them light of the upper sensor 28, and then further drops down to interrupt the light of the lower sensor 29. The upper and lower sensors 28, 29 produce signals, and the CPU 19 counts the number of gauzes passing through the hopper 26 according to the time relational signals. That is, the CPU 19 only counts the number when the lower sensor 29 produces a detection signal within a predetermined interval after the upper sensor 28 produced a detection signal. The count indicator 22c of the display unit 22 indicates the counted number.

The gauze 12 further drops down into the bag 23 in the container 25 which is disposed on the weighing table 16. The weighing table 16 measures the total weight of the container 25 including the bag 23 and the gauzes 12 by the load cell 16a and outputs a voltage signal. The CPU 19 calculates the amount of the blood absorbed in the gauzes 12 by a following process;

(a) The tare weight including the container 25 and the bag 23 is substrated from the total weight measured by the weight sensor 16a.

(b) The net weight of the gauzes 12 in the container 25 is obtained by multiplying a unit dry weight of the gauze 12 to the number of gauzes 12 counted.

(c) By substrating the latter from the former, weight of blood absorbed in the gauzes 12 is obtained.

(d) The volume of blood is calculated by dividing the weight value with the specific gravity of blood and is indicated on the blood amount indicator 22a of the display unit 22.

The CPU 19 of the present embodiment is provided with logical functions as described below to prepare for possible problems occurring during surgery as follows.

(1) A gauze 12 sticks to the inner surface of the hopper 26:

In this case, a gauze 12 may continue to stay there without interrupting the light of the sensors 28, 29, or hang down from the hopper 26 so as to continue to interrupt light of the sensors 28, 29. In the former case, the operator can pick up the gauze 12 by inserting a hand into the hopper 26 and drop it again. In the latter case, an alarm signal is produced, and the counting lamp 22b continues to light so that the operator notices an abnormal condition. When the alarm is canceled, the counting and measuring operation resumes.

(2) More time than the predetermined value (0.5 sec for example) has passed after detection by the upper sensor 28 without being detected by the lower sensor 29:

In this case, the apparatus cannot count and the alarm is activated. By canceling the alarm after removing the gauze 12 and dropping it, the operation is resumed.

(3) Gauze 12 pile up to a height to keep interrupting any one of the sensors 28, 29.

In this case, the apparatus cannot count and the alarm is activated. The operator may insert a hand into the hopper 26 to equalize the distribution of the gauzes in the container 25 so that they do not interrupt the sensors 28, 29. Thus, the alarm is canceled and operation is resumed. The operator's hand is not counted by the CPU 19 since the hand keeps on interrupting the upper sensor 28 until it is withdrawn above the upper sensor 28, and the CPU 19 judges this is an abnormal case.

When the operator cancels the alarm after the gauze 12 is removed, alarm will be turned off after the predetermined lapse of time (0.5 sec for instance), and the counting and measuring condition becomes normal. The data including the sum of used gauzes 12, sum weight of blood and sum volume of blood are stored in the RAM 21 while alarm is on, and is recalled when alarm is canceled. The counting and measuring operation starts again by adding the data of newly counted and measured values to the recalled data.

As is described above, the CPU 19 is designed to count a gauze 12 only when it receives time series relational signals indicating that the upper sensor 28 first senses an object and then the lower sensor 29 senses an object. In such a case, the CPU 19 determines conditions normal and does not produce any alarm signal. On the other hand, when the upper and lower sensors 28, 29 sense an object simultaneously, or when the lower sensor 29 senses an object before the upper sensor 28, the CPU 19 determines that conditions are not normal and does not count. When the operator inserts a hand into the hopper 26 and retracts it, the detection signal is produced first by lower sensor 29 since the detection signal is produced when interrupted light has recovered. Therefore, this condition is judged to be abnormal and is not counted by the CPU 19.

When the surgical operation is over and the number of the gauzes 12 are confirmed, the bag 23 is closed by pulling the string. The bag 23 including the used gauzes 12 is drawn out of the envelope 11 through the door 13 without any difficulty.

According to the above embodiment, the number of gauzes 12 and the volume of blood absorbed therein is obtained automatically from the data of the pass detection sensor 40 and the weight sensor 16a without errors. In an abnormal case such as sticking or hanging of the gauze 12 on the inner wall of the apparatus, the operator can remove and drop it by a hand. It is unnecessary to recount the gauzes 12 or to reset the display of the apparatus. The results of counting or measuring is displayed at the display unit 22. The subject of display such as the number of used gauzes 12, individual weight of gauzes 12 dropped in the container 25 or calculated volume of blood can be selected by switching the button switches on the liquid crystal display of the display unit 22.

The weighing table 16 may be conveniently used for weighing other objects because the container 25 can be easily removed from the side door 13 of the envelope 11. Further, since casters 15 are provided to the envelope 11, the apparatus is convenient for transportation to the necessary places.

SECOND EMBODIMENT OF THE INVENTION

The second embodiment of the present invention will be described below referring to FIGS. 10 to 16. The second embodiment is comprised of the same elements as the first embodiment as described above except for the elements described below.

Figure 11:
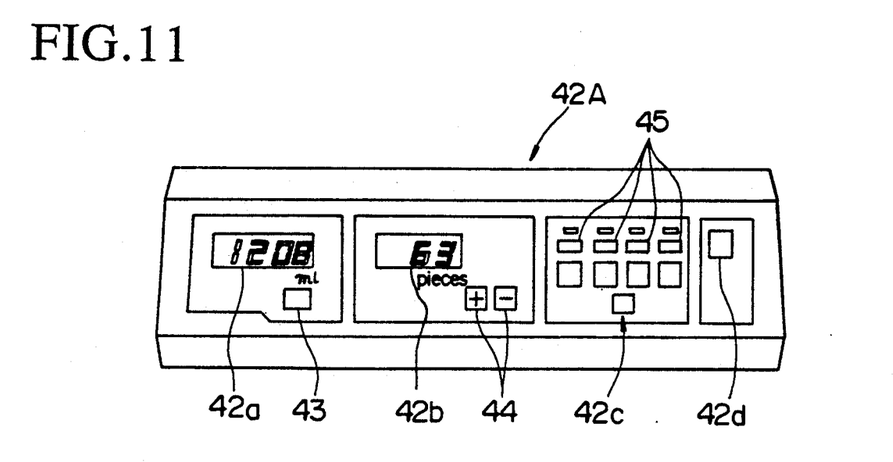
FIG. 11 is an enlarged view of the control panel of the apparatus of FIG. 10.
Figure 12:
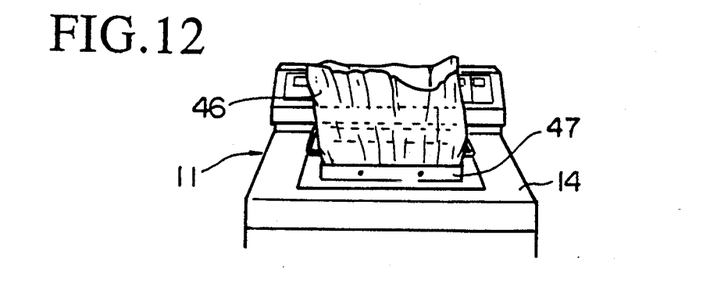
FIG. 12 is a perspective view of the apparatus of FIG. 10.
Figure 13:
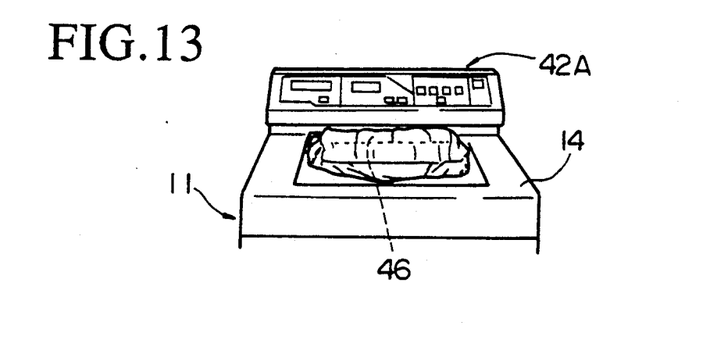
FIG. 13 is another perspective view of the apparatus of FIG. 10.

The control panel 42a comprises a blood amount indicator 42a, to which a switching button 43 for displaying a plurality of alternative modes is provided. For example, in a first mode, the blood amount indicator 42a indicates the total blood amount, in a second mode, it indicates the blood amount per gauze, in a third mode, it indicates the blood amount per time (minute). A count indicator 42b for indicating the number of gauzes comprises a correcting switch 44 for manually correcting the counted number in an abnormal case. Numeral 42c depicts a gauze counter capable of indicating the dry weight of several types of gauzes (an example including four types is shown), which comprises selection buttons 45 for selecting the type of gauze 12 from several predetermined ones, for example, weighing 3g, 4g, 5g and 6g. The type of gauzes 12 is entered in the memory of the CPU 51 as values of dry weight of the gauze 12 prepared for the operation. The type of gauze 12 is determined according to what kind of operation is to be done. Numeral 42d depicts a resetting button for resetting the indicators to zero. However, the invention is not restricted by such values of dry weight or number of selection.

At the aperture of the upper plate 14 of the envelope, a frame 47 for fixing the edge of a covering sheet 46 thereto is provided. The covering sheet 46 is provided for preventing the apparatus from being contaminated with blood. The hopper 48 of the embodiment is made in a rectangular trapezoidal shape.

Significant differences of the present embodiment from the first embodiment exist in the construction of the pass detection sensor 50 and the function of the CPU 51.

Figure 14:
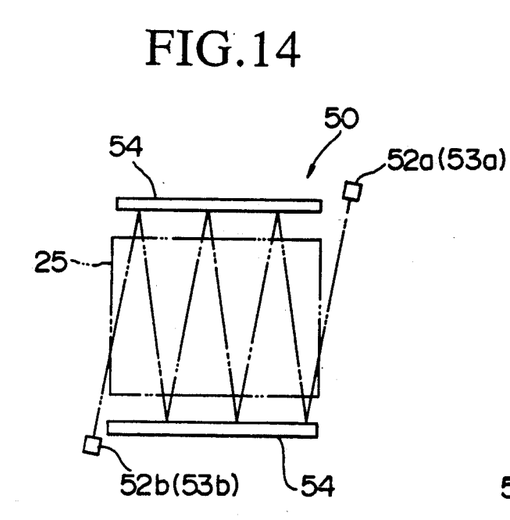
FIG. 14 is a cross-sectional view of the apparatus of FIG. 10.
Figure 15:
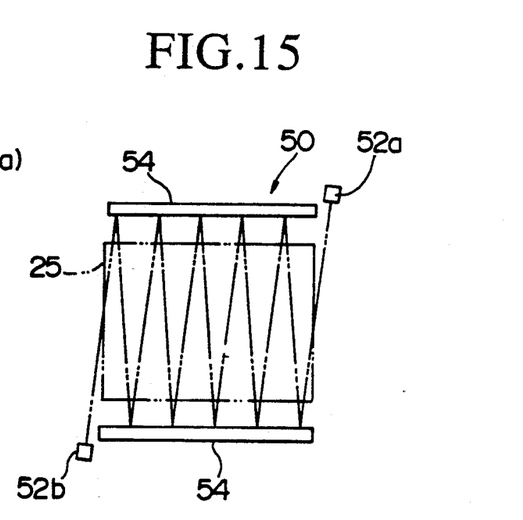
FIG. 15 is another cross-sectional view of the apparatus of FIG. 10.

The pass detection sensor 50 is comprised of an upper and lower sensors 52, 53, each of which is comprised of a light projector 52a, 53a, a light receiver 52b, 53b and two light reflectors 54 arranged around the passage. Each pair of the light projector 52a, 53a and the light receiver 52b, 53b are arranged in parallel and not on a same line as described in the first embodiment. The light reflectors 54 have mirror surfaces 54a arranged in parallel so as to guide a light of the light projector 52a, 53a to the light receiver 52b, 53b after several reflections. By such construction, a light of one light projector 52a, 53a runs in a staggered manner to cover the whole area of the passage. Therefore, the apparatus prevents the occurrence of unsensed passing of an object so that it increases the reliability of the apparatus. Thus, the area of the bottom end of the hopper 48 can be enlarged so as to lessen the possibility of hanging of a gauze 12. Since it is accomplished through provision of mirrors 54, not of expensive sensors, the increase of cost is small.

Figure 16:
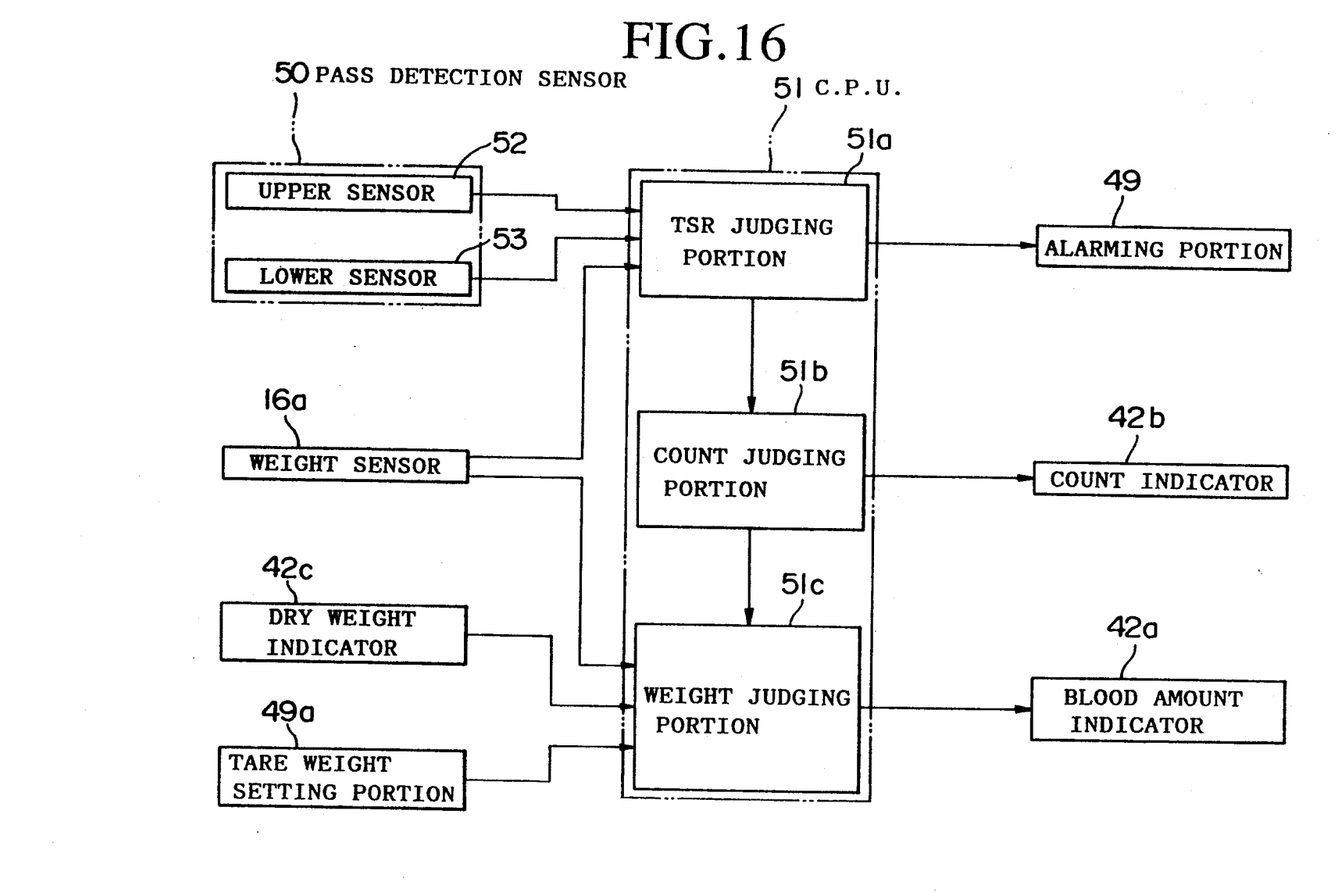
FIG. 16 is a schematic diagram of the controlling system of the apparatus of FIG. 10.

The function of the CPU 51 of the apparatus is shown in a schematic diagram in FIG. 16. The CPU 51 judges a TSR between signals of the pass detection sensor 50 and the weight sensor 16a at the TSR judging portion 51a. The CPU 51 analyzes the lapse time during the light is interrupted at its TSR judging portion 51a, and judges whether it is longer than the predetermined value. When it is longer than 0.5 sec, for example, the CPU 51 determines that the TSR is abnormal and produces an alarm signal to the alarming portion 49 such as a buzzer. It also judges whether the time interval between the sensings by the pass detection sensor 50 and the weight sensor 16a is within the predetermined value (0.5 sec for example).

The TSR judging portion 51c also judges the pattern of the output signal of weight sensor. When the pass detection sensor 50 senses a dropping object, the CPU 51 starts to install the output signal of the weight sensor 16a into the RAM 21 continually, i.e., once in every predetermined interval of time (measuring interval, 0.1 sec for example) during a predetermined period (measuring period, 1.0 sec for example). The measuring period is determined with reference to the usual interval time between dropping of the gauzes by an operator. According to the experimental result, the interval time was measured to be 2 seconds at the minimum. A series of weight data is recognized as a time series relational signals, i.e., a signal pattern. The CPU 51 compares the pattern of TSR signal with the typical pattern installed in the RAM 21 as a reference pattern, which was typical when a dropped gauze 12 is received in the container 25. If the recognized pattern is different by a certain degree from the reference pattern, the CPU 51 judges it to be abnormal. In a case when an outer object bumps to the envelope 11, the weight sensor 16a produces a pattern of signals different from the reference pattern, and is neglected by the CPU 51.

The value indicated by the weight sensor 16a itself is also judged by the CPU 51 at its weight judging portion 51c. The increase of weight is calculated by the CPU 51 by comparing the weight value currently measured with a value measured last time. If the increased value is less than the predetermined value such as dry weight of the gauze 12 for example, it is judged to be abnormal, and is not counted as one drop of gauze 12. The CPU 51 judges that it is a drop of blood and adds it to the blood weight.

Further, The CPU 51 judges abnormal when the increased weight sensed by the weight sensor 16a becomes zero at the end of the measuring period, because it is caused by a vibration transmitted to the apparatus.

When the increased value is more than the predetermined value, and the TSR judging portion 51a judges other features to be normal, an output signal is produced to the count judging portion 51b. The count judging portion 51b counts a drop of a gauze 12 according to the output signal of the TSR judging portion 51a and produces an output signal to the count indicator 42b and the weight judging portion 51c of the CPU 51. The weight judging portion 51c further calculates the weight of absorbed blood from the output signals from the count judging portion 51b, the weight sensor 16a, the dry weight indicator 42c and tare weight setting portion 49a in the same manner as the first embodiment and produces it to blood amount indicator 42a.

The control panel 42a is set to zero by pushing the resetting switch 42d so as to display the data from newly dropped gauzes after then. If plurality of gauzes 12 are dropped or wrong object is dropped by accident, the data can be amended by pushing the correction button switch 44.

In this embodiment, the CPU 51 judges the TSR of the output signals of the pass detection sensor 50 and the weight sensor 16a, so that it can judge the condition of the apparatus in more detailed than the first embodiment. Therefore, the counting and measuring operation is done with a high reliability.

OTHER EMBODIMENTS OF THE INVENTION

Other embodiments of the present invention will be described below referring to FIGS. 17 to 21. The embodiments described below is made as an improvement for the auxiliary parts of the apparatus, and the main construction is the same as the first or second embodiment as described above.

Figure 17:
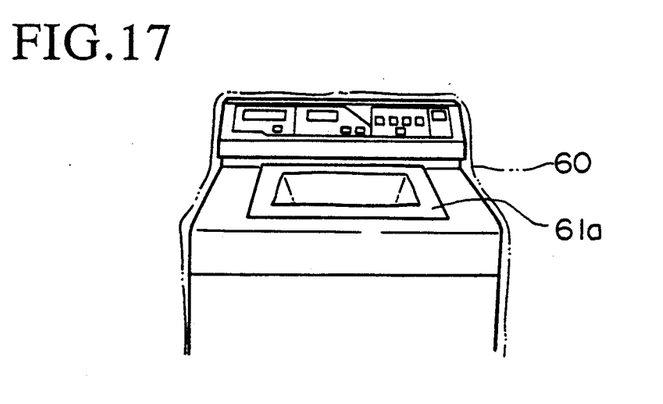
FIG. 17 is a perspective view of the apparatus according to the third embodiment of the invention.
Figure 18:
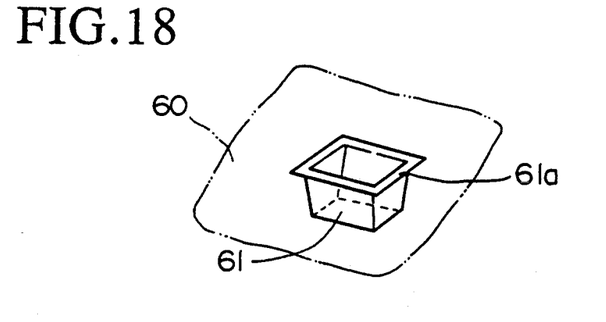
FIG. 18 is a perspective view of a part of the apparatus of FIG. 17.

FIGS. 17 and 18 depict a third embodiment of the present invention, characterized in comprising a covering sheet 60 capable of covering the apparatus. The covering sheet 60 is formed from a paper or a transparent material such as polyethelene or polypropylene. The covering sheet 60 is formed to have an aperture corresponding to that of hopper 61. The inner edge portion of the sheet 60 is integrally adhered to an upper edge 61a of the hopper 61. The covering sheet 60 is extended over the apparatus so as to cover the control panel 42a. By such construction, the apparatus can be used without being touched by unclean hands of the operator. The operator who treats gauzes 12 is able to operate the apparatus without contaminating the apparatus and without being helped by other person. Since a chance for the apparatus of being contaminated is decreased, the necessity for sterilization of the apparatus can be reduced. Since the bag 60 is non-returnable, the trivial work of the operator can be saved.

Figure 19:
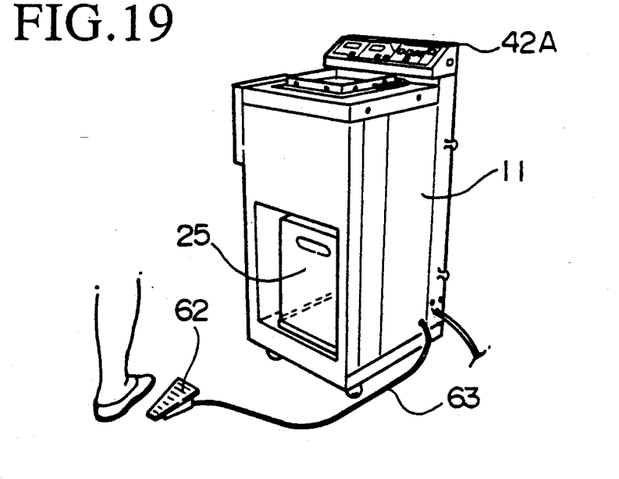
FIG. 19 is a perspective view of the apparatus of according to the fourth embodiment of the invention.

FIG. 19 depicts a fourth embodiment of the invention, characterized in comprising a foot switch 62 for operating the apparatus. The foot switch 62 is connected via a electric cable 63 to the control unit in the envelope 11. The foot switch 62 can be used in various ways including resetting the control panel 42a, correcting the displayed value, switching the displayed subject etc. By such a construction, the same effects are obtainable as the third embodiment.

Figure 20:
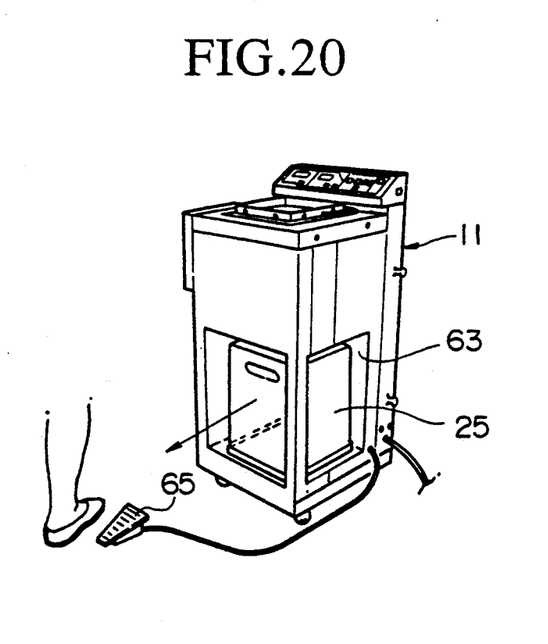
FIG. 20 is a perspective view of the apparatus according to the fifth embodiment of the invention.
Figure 21:
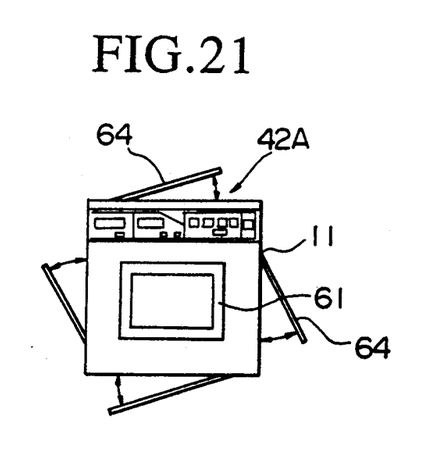
FIG. 21 is a plan view of the apparatus of FIG. 20.

FIGS. 20 and 21 depicts a fifth embodiment of the invention, characterized in that the envelope 11 comprises a plurality of apertures 63 for drawing out or inserting the container 25 therethrough. These apertures are covered with doors 64, as shown in FIG. 21, which are operable by a foot switch 65. By such construction, the operator can treat the container 25 in a case of exchanging it without touching the apparatus, so that the envelope 11 is not contaminated. Further, since a plurality of doors 64 are provided, the operator can choose one of them for convenient one suitable to the circumstance. It is helpful for the operator because it is unnecessary to move the apparatus to change its direction.

What is claimed is:

1. An apparatus for counting dropping objects comprising:
   an envelope defining a hollow passage for passing dropping objects therethrough, said envelope including an entrance portion for guiding said objects to said passage, said entrance portion having an upper and a lower section, and being tapered with said upper section having a cross-sectional area larger than a cross-sectional area of said lower section, said lower section having an elliptical bottom aperture;

a plurality of sensors disposed at said passage spaced at a vertical distance from each other for sensing said dropping objects;

a counting means for counting said dropping objects according to output signals of said sensors;

a judging means for judging whether a counting condition is normal or not according to the time series relationship of said output signals; and an alarm means for producing alarm signals when said judging means judges that said condition is abnormal.

2. A counting apparatus according to claim 1, wherein each of said sensors comprises a light projector and a light receiver located at opposite sides of said hollow passage.

3. A counting apparatus according to claim 2, wherein said judging means judges according to a lapse of time during which each said light receiver does not receive light from each corresponding light projector.

4. A counting apparatus according to claim 2, wherein each of said sensors further comprises a reflecting means arranged at said hollow passage for reflecting light from said light projector to said light receiver.

5. A counting apparatus according to claim 4, wherein said reflecting means comprises two mirrors arranged at the opposite sides of said hollow passage.

6. A counting apparatus according to claim 3, wherein said judging means judges according to an interval of time between said output signals.

7. A counting apparatus according to claim 1 further comprising a display means for indicating an output of said counting means.

8. An apparatus for counting used medical cloths and measuring the quantity of liquid absorbed therein comprising:

an envelope defining a hollow passage for passing said medical cloths therethrough;

an entrance portion for guiding said medical cloths to said passage;

a pass detection sensor arranged at said passage for sensing said medical cloths and generating a pass output signal;

a weight sensor disposed at the bottom of said passage for sensing a weight of dropped medical cloths and generating a weight output signal;

a control unit for operating on said output signals to output the number of said dropped medical cloths and the weight of liquid absorbed therein, said control unit comprising a judging means for judging whether said output signals are normal or not according to the time series relationship of said output signals; and an alarm means for producing alarm signals when said judging means judges said output signals are abnormal.

9. A counting and measuring apparatus according to claim 8, wherein said control unit judges whether a counting or measuring condition is normal or not by comparing the time series relationship of said output signals with a predetermined referential signal pattern.

10. A counting and measuring apparatus according to claim 8, wherein said control unit produces a control signal when said judging means judges that said output signals are abnormal.

11. A counting and measuring device according to claim 8 wherein said control unit stops operating on said pass output signal when said judging means judges that said output signals are abnormal.

12. A counting and measuring apparatus according to claim 8, wherein said pass detection sensor comprises a light projector and a light receiver.

13. A counting and measuring apparatus according to claim 12, wherein said pass detection sensor further comprises a reflecting means for reflecting light from said light projector to said light receiver.

14. A counting and measuring apparatus according to claim 13, wherein said reflecting means comprises two mirrors arranged parallel to each other.

15. A counting and measuring apparatus according to claim 8 further comprising a display means for indicating the output of said control unit.

16. A counting and measuring apparatus according to claim 8 further comprising an input means for inputting selected operating parameters for said control unit.

17. A counting and measuring apparatus according to claim 8, further comprising a container and a bag installed in said container for receiving said medical cloths therein.

18. A counting and measuring apparatus according to claim 8, wherein said envelope has an upper portion, and wherein a covering sheet is provided for covering said upper portion, said covering sheet having an aperture for accommodating said entrance portion.

19. A counting and measuring apparatus according to claim 8 further comprising a housing having a plurality of side doors, a container disposed in said housing for collecting said dropped medical cloths and a foot switch for opening said side doors to remove said container.

20. A counting and measuring apparatus according to claim 8 further comprising a foot switch coupled to said control unit.

* * * * *